United States Patent [19]

Nepom et al.

[11] Patent Number: 5,196,308
[45] Date of Patent: Mar. 23, 1993

[54] METHODS FOR IDENTIFYING THE DQW3.2 ALLELE ASSOCIATED WITH INCREASED RISK OF INSULIN-DEPENDENT DIABETES MELLITUS

[75] Inventors: Gerald T. Nepom; Barbara S. Nepom, both of Bainbridge Island, Wash.

[73] Assignee: Genetic Systems Corporation, Redmond, Wash.

[21] Appl. No.: 325,058

[22] Filed: Mar. 13, 1989

Related U.S. Application Data

[63] Continuation of Ser. No. 745,321, Jun. 14, 1985, abandoned.

[51] Int. Cl.$^5$ ............... G01N 33/543; G01N 33/564; G01N 33/577
[52] U.S. Cl. ................... 435/7.21; 435/7.24; 435/7.9; 435/948; 436/506; 436/518; 436/530; 436/531; 436/548; 436/800; 436/804; 436/809; 436/811; 436/821; 935/110
[58] Field of Search ............ 435/7, 172.2, 240.26, 435/240.27, 948, 70.21, 68, 7.21, 7.24, 7.9; 436/501, 519, 531, 548, 800, 804, 809, 811, 821, 506, 518, 530; 935/110

[56] References Cited

PUBLICATIONS

Schreuder, G. M. T. 1984. HLA-DR, DQ, and Dw Relationships. In: Histocompatibility Testing 1984. E. D. Albert et al. Editors Springer-Verlag, Berlin, p. 243.
Schreuder, G. M. T. et al. HLA-DR, DQ, LB, and TA10 Specificities of Ninth Workshop Homozygous Typing Cells. In: Histocompatibility Testing 1984. E. D. Albert et al. Editors. Springer-Verlag, Berlin. pp. 243-248.
Duquesnoy, R. J. et al. 1984. Antigen Report: HLA-DQw3. In: Histocompatibility Testing 1984. E. D. Albert et al. Editors Springer-Verlag, Berlin. pp. 209-211.
Shannon, A. D. et al. 1984. Characterisation of the HLA-D Region DQw3 Specificity Using the Monoclonal Antibodies 2HB6 and IVD12. In: Histocompatibility Testing 1984. E. D. Albert et al. Editors. Springer-Verlag, Berlin. pp. 439-442.
Owerbach, D. et al. 1983. HLA-D Region β-Chain DNA Endonuclease Fragments Differ Between HLA-DR Identical Healthy and Insulin-Dependent Diabetic Individuals. Nature 303:815-817.
Cohen-Haguenauer, O. 1985. A Systematic Study of HLA Class II-β DNA Restriction Fragments in Insulin-Dependent Diabetes Mellitus. Proc. Nat'l. Acad. Sci. USA 82:3335-3339.
Kim, S. J. 1985. Identification of a Polymorphic Variant Associated with HLA-DQw3 and Characterized by Specific Restriction Sites Within the DQ β-Chain Gene. Proc. Nat'l. Acad. Sci. USA 82:8139-8143.
G. C. Baldwin et al., Electrophoretic Variation Between Class II Molecules Expressed on HLA-DRw8 Homozygous Cells Reveals Multiple Distinct Haplotypes. Immunogenetics, 21:49-60, 1985.
G. T. Nepom et al., Multiple Ia-Like Molecules Characterize HLA-DR2-Associated Haplotypes Which
(List continued on next page.)

Primary Examiner—David A. Saunders
Attorney, Agent, or Firm—Townsend and Townsend

[57] ABSTRACT

Methods for identifying individuals at increased risk of diabetes are disclosed. The methods disclosed utilize the discovery of the DQw3.2 variant, which identifies a specific allelic polymorphism at a sinle gene locus. One preferred method utilizes a labeled probe to detect the DQw3.2 allele. This method involves estimating the size of the hybridizable DNA fragment generated by a specific restriction endonuclease and therefrom determining the presence of the allele. A second preferred method involves the serologic detection of the DQw3.2 allele. Within this method, immunocomplexes formed between two different MAb's and separate portions of a cell collection are detected and the presence or absence of the allele determined.

11 Claims, 2 Drawing Sheets

OTHER PUBLICATIONS

Differ in HLA-D, *Human Immunology* 10:143–151, 1984.

G. T. Nepom et al., The HLA-DR4 Family of Haplotypes Consist of a Series of Distince DR and DS Molecules, *J. Exp. Med.,* 159:394–404, 1984.

G. T. Nepom et al., A Locus-Specific Oligodeoxynucleotide Probe Specific for HLA Class II DQ Beta Genes. *Advances in Gene Technology: Molecular Biology of the Immune System,* ICSU Press, pp. 259–260, 1985.

B. Nepom et al., Characterization of Specific HLA-DR4-Associated Histocompatibility Molecules in Patients with Juvenile Rheumatoid Arthritis, *J. Clin. Invest.,* 74:287–291, 1984.

S. Holbeck et al., HLA-DR4-Associated Haplotypes are Genotypically Diverse within HLA, *J. Immunol.,* 135:637–641, 1985.

■ DQ46 oligo site

METHODS FOR IDENTIFYING THE DQW3.2 ALLELE ASSOCIATED WITH INCREASED RISK OF INSULIN-DEPENDENT DIABETES MELLITUS

This is a continuation of application Ser. No. 745,321, filed Jun. 14, 1985, now abandoned.

DESCRIPTION

1. Technical Field

The present invention relates generally to the disease known as insulin-dependent diabetes mellitus, and more specifically, to methods for identifying individuals at increased risk of diabetes.

2. Background Art

Diabetes mellitus is a complex syndrome (or syndromes) characterized by hyperglycemia, thickening of basement membrane of the capillaries, and a variety of late complications including accelerated atherosclerosis, retinopathy, nephropathy, and neuropathy. (Parker, Clinical Immunology, V.II, 1980). Diabetes may include any or all of the above syndromes, and affects approximately 2% of the U.S. population. Approximately 1 in 4 of these cases is insulin-dependent, referred to as IDDM, usually present in individuals below the age of 30, with the rapid onset of glucose intolerance.

While it is generally accepted that hereditary factors are important in the etiology of diabetes, the exact genetic mechanisms involved are not understood. The search for a genetic marker for susceptibility to diabetes had been unfruitful until 1973-74 when investigators first called attention to the relationship between diabetes and the major histocompatibility complex in man, called HLA.

The HLA antigens are encoded by four loci on chromosome six, designated A, B, C and D. Most associations between HLA and disease susceptibility have involved the D region of HLA. This locus was originally defined as the genetic region mismatch at which causes stimulation in a one-way mixed lymphocyte reaction (MLR). Human Ia antigens map to the HLA-D region. These appear to be encoded by at least three distinct loci, DR, DQ and DP, each with its distinct alpha and beta chains.

Each HLA-DR alloantigenic specificity (DR1-w14) represents a serologically defined reaction pattern between well-characterized antisera and major histocompatibility complex (MHC) class II molecules. Accordingly, each specificity corresponds to a particular epitope recognized by an alloantiserum which is present on HLA-D-encoded cell surface molecules.

Among the HLA specificities, HLA-DR4 is the most interesting. This antigen has been found to occur more frequently in patients with adult rheumatoid arthritis, insulin-dependent diabetes, and some forms of juvenile rheumatoid arthritis than in the general population. However, analysis of the relationship between HLA-DR specificities and individual class II molecules expressed on homozygous typing cells has shown that structurally distinct molecules may be serologically indistinguishable. The implication of this finding is that what DR4+ cells have in common is the DR4 epitope carried by at least one of their D-region gene products which reacts with the DR4 alloantiserum to give a positive typing reaction. Beyond this cross-reactive epitope, however, each cluster of cells possesses a unique collection of class II antigens, such that "DR4" encompasses multiple distinct haplotypes. If specific haplotypes account for HLA associations with disease, then the serologic HLA specificity alone is not a sufficiently specific marker to optimally predict disease risk.

Restriction endonuclease digestion of genomic DNA may be used to identify specific nucleotide sequences, the presence or absence of which can function as markers for individual genes or gene segments. Fragments which hybridize to a single probe can sometimes be assigned to specific genes. When such a fragment is variably expressed in different individuals, it is referred to as "polymorphic" and can potentially relate to functional differences.

Investigators have previously reported a large number of restriction endonuclease fragment polymorphisms (RFLP) which exhibit some correlation with diabetes, hybridizing to DQB probes. (Cohen-Haguenauer, et al., PNAS 82: 3335-3339, 1985; Owerbach, et al., Nature 303: 815-817, 1983.)

Despite these advances in understanding the genetic mechanisms involved in susceptibility to diabetes, the disease is currently diagnosed on the basis of clinical presentation and laboratory tests. Clinical presentation can range from the obvious to the bewildering, depending on which symptoms appear first. Laboratory tests consisting of measurements of glucose and insulin and its precursors in the blood of patients, before and after challenge of the patient with glucose itself, are diagnostic. Heretofore, noticeably absent from the art has been the clinical ability to identify individuals who are at increased risk of diabetes prior to the onset of symptoms.

The ability to identify individuals at increased risk of diabetes could have several important applications. It could be used within families of individuals with known diabetes in order to predict which other family members are at risk. Second, it could be used with individuals who exhibit diabetic symptoms in the context of other, more complex diseases, in an attempt to identify whether the individual has "traditional" diabetes which may be treated conventionally. Finally, should the identification of a risk factor for IDDM have sufficient predictive value, it can be anticipated that clinicians would use it within a screening test to identify individuals at increased risk for the disease.

The present invention provides methods satisfying this need in the art for identifying individuals at increased risk of diabetes, and further provides other related advantages.

DISCLOSURE OF THE INVENTION

Briefly stated, the present invention discloses methods for identifying individuals at increased risk of diabetes. One aspect of the invention essentially involves the steps of (a) incubating a first monoclonal antibody (MAb) reactive with DQw3.2 and DQw3.1 with a portion of a cell collection; (b) incubating a second monoclonal antibody reactive with DQw3.1 with a separate portion of the cell collection; (c) detecting the presence of immunocomplexes formed between the first MAb and the cells, and the second MAb and the cells; and (d) determining from the results of the step of detection whether haplotypes associated with susceptibility to diabetes, such as the DQw3.2 haplotype, are present. In a preferred embodiment of this method, the first MAb is P100.1 and the second MAb is A10, positive reactivity with P100.1 and negative reactivity with A10 indicating the presence of a haplotype associated with susceptibility to diabetes.

A second aspect of the present invention involves a method for detecting the presence of a specific allele correlated with an increased risk of diabetes. The method comprises: (a) digesting DNA purified from a cell collection with a restriction endonuclease to generate DNA fragments; (b) separating the DNA fragments on the basis of size; (c) hybridizing the separated fragments with a labeled probe substantially homologous with the DQB gene of HLA; and (d) detecting the signal from the hybridized probe, and therefrom determining the presence or absence of the allele. In a preferred embodiment of this method, the probe is comprised of the sequence GGAGCCCACAGTGACCATC.

Other aspects of the invention will become evident upon reference to the following detailed description and attached drawings.

BEST MODE FOR CARRYING OUT THE INVENTION

Within the present invention, applicants have found that there are multiple distinct DQ alleles within DR4+ haplotypes, and that specific haplotypes, rather than the serologic marker, identify disease susceptibility.

One of the DQB genes, referred to as "$DQB_1$," is relatively nonpolymorphic among individuals with similar DQ serologic typing specificities. The other DQB locus, referred to as "$DQB_2$," is polymorphic among individuals who are serologically indistinguishable using conventional typing sera. Two stable $DQB_2$ allelic variants exist which encode polypeptides carrying DQw3 specificities. These two $DQB_2$ allelic variants differ from each other throughout a large portion of their genomic DNA, as evaluated by restriction mapping using a synthetic oligonucleotide probe specific for the B2 exon.

Upon analysis of 17 unrelated HLA DR4+ IDDM patients for genomic DQB polymorphisms, 16 exhibited a characteristic RFLP pattern for one of these specific $DQB_2$ allelic variants, and not the other. This variant, referred to as "DQw3.2," therefore serves as a specific genomic marker for $DQB_2$ genes on haplotypes carrying the DR4 serologic specificity, which are associated with IDDM. This specific variant includes some RFLP, such as a DQB 12.0 kb Bam HI and 1.9 kb Taq I fragments which were observed by other investigators in patients with diabetes, as noted above.

Through the mapping of such nucleotide variation to a specific region of an expressed DQB gene, applicants have strongly implicated this gene product or a closely linked product in disease susceptibility. The DQw3.2 variant identifies a specific allelic polymorphism at a single gene locus.

The present invention, through the discovery of the DQw3.2 variant, provides two basic methods of identifying individuals at increased risk of diabetes. The first of these methods involves the use of a labeled probe to detect the DQw3.2 allele. The second of these methods involves the serologic detection of the DQw3.2 allele.

A. Use of a Labeled Probe in the Diagnosis of DQw3.2

As noted above, the two $DQB_2$ allelic variants differ from each other throughout a large portion of their genomic DNA. Six different restriction endonucleases, including Bam HI, Pvu II, Hind III, Xba I, Taq I, and Sst I are all capable of recognizing this allelic difference within the method of the present invention.

Figure 1:
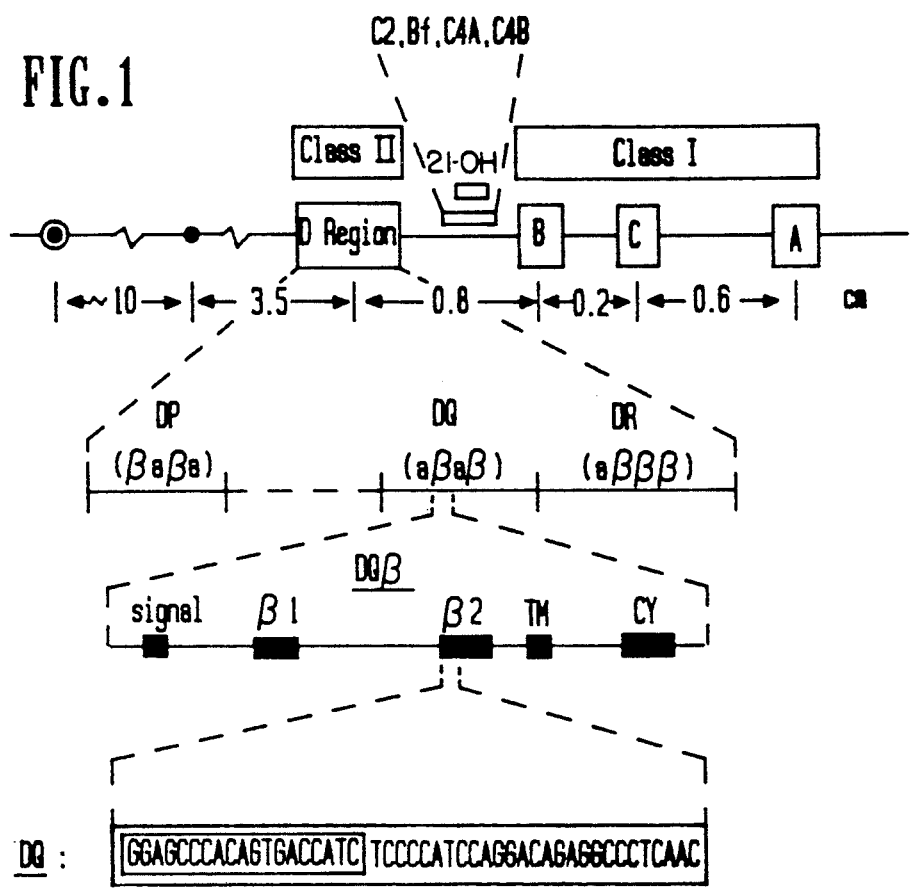
FIG. 1 is a schematic illustrating the genomic location from which the probes of the present invention were derived.

After purification of DNA from an individual of interest, digestion with one of the restriction endonucleases noted above may be performed. Following digestion, samples are electrophoresed on agarose gels in Tris acetate EDTA buffer. Subsequent to electrophoresis, the gels are dried on a vacuum gel dryer and the dried gels inserted in a polyethylene bag in the presence of radio-labeled probe DNA. Alternatively, Southern blot procedures may be used in which the gels are blotted onto nitrocellulose or nylon derivatized membranes. Such membranes may then optionally be UV-irradiated, and may be pre-hybridized with solutions containing nonradioactive RNA or DNA, before hybridization with labeled probe DNA. The sequence of the oligonucleotide probes used within the present invention is shown in FIG. 1. As shown in FIG. 1, preferred sequences include (a) GGAGCCCACAGTGACCATC; and (b) GGAGCCCACAGTGACCATCTCCCCATCCAGGACAGAGGCCCTCAAC.

The probe can be labeled with a radioisotope or an enzyme. Where the label is an enzyme, the enzyme can be conjugated directly to the probe, or indirectly via an avidin-biotin bridge (Singer & Ward, PNAS 79: 7331; Pengolizzi, et al., in Advances in Gene Technology: Human Genetic Disorders, ed. F. Ahmad). Hybridization is detected by adding the appropriate substrate(s), cofactor(s) and/or chromogen(s) for the enzyme.

After the probe DNA is synthesized, it can be labeled with, for instance, P32. In this exchange reaction, an $\alpha$P32 is provided at the 5' terminus of the oligonucleotide. The labeled oligonucleotide is diluted appropriately and incubated with the dried gel in the polyethylene bag under conditions which favor hybridization. After a sufficient length of time, the dried gel is removed, washed and subsequently exposed to x-ray film to reveal by autoradiography the presence of hybridizing bands. The size of the hybridizing fragments is then estimated relative to molecular weight standards.

Figure 2:
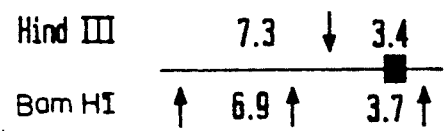
FIG. 2 illustrates the structural difference between DQw3.1 and DQw3.2 at $DQB_2$.
Figure 2:
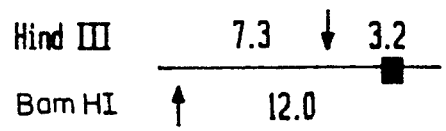

Referring now to FIG. 2, it can be seen that the presence of the DQw3.2 allele can be distinguished from the presence of the DQw3.1 allele by the appearance of a 3.2 kb band and the absence of a 3.4 kb band when the purified DNA is digested with Hind III.

Alternatively, when using the restriction endonuclease Bam HI, DQw3.2 can be distinguished from DQw3.1 by the appearance of a 12.0 Kb band and the absence of 6.9 Kb and 3.7 Kb bands. Comparable differences may be identified when using the other restriction endonucleases described above, as follows:

|          | DQw3.1   | DQw3.2   |
| -------- | -------- | -------- |
| Pvu II - | 3.55 kb  | 3.45 kb  |
| Xba I -  | 5.7 kb   | 2.35 kb  |
| Taq I -  | 4.55 kb  | 1.9 kb   |
| Sst I -  | 2.4 kb   | 2.2 kb   |

B. Serologic Detection of the DQw3.2 Allele

Within a preferred embodiment of this method of the present invention, two monoclonal antibodies, designated P100.1 and A10, are used to identify the DQw3.2 allele. Antibody P100.1 is a monoclonal antibody raised by fusion of mouse spleen cells immunized with human lymphoblastoid cell lines, with the myeloma NS-1, to yield hybridomas secreting monoclonal antibody directed against an epitope associated with the HLA-DQw3 specificity. This antibody forms a part of the basis for pending U.S. Pat. No. application, Ser. No. 740,120, now abandoned, filed May 31, 1985, the text of which is herein incorporated by reference, and has been deposited with the ATCC under Accession No. HB-8822. Antibody A10 is a monoclonal murine antibody available from Dr. Hiroo Maeda, Tokyo Blood Transfusion Service, Tokyo, Japan. The use and characterization of this antibody in screening HLA-typed populations has been described (Bodmer, et al. Histocompability Testing 1984, eds. Albert, Baur and Mayr (Springer-Verlag, Berlin) pp. 217-236; Maeda, H. Tissue Antigens 23: 163-170, 1984).

The antibodies described above may be used in cytotoxicity assays, and also in binding assays, including but not limited to, ELISA, micro-ELISA, as identified in pending U.S. patent application Ser. No. 740,120, now abandoned, and fluorescence and radioimmune assays. Within any of these formats, cells from an individual or a patient are mixed with the antibodies separately, followed by the detection procedure (whether isotope, fluorescence, chromogen, or complement) and then analyzed for reactivity. Positive reactivity with P100.1 and negative reactivity with A10 constitute the identification and diagnosis of the DQw3.2 allele. Reactivity with both antibodies constitutes diagnosis of the DQw3.1 allele. Nonreactivity with both antibodies constitutes exclusion of both DQw3.1 and 3.2 alleles.

Alternatively, the antibodies may be coated onto separate portions of a surface, such as plastic or filter paper, and the surface reacted with cells from an individual of interest. The surface is washed to remove unbound cells, and the bound cells then visualized by staining either with a protein stain, such as coomassie blue, or with a second, labeled antibody.

To summarize the examples which follow, Example I demonstrates the use of a labeled probe in the diagnosis of DQw3.2. Example II demonstrates the serologic detection of the DQw3.2 allele.

The following examples are offered by way of illustration and not by way of limitation.

EXAMPLES

Example I

Use of a Labeled Probe in the Diagnosis of DQw3.2

Homozygous Cell Lines (HCL): EBV-transformed B lymphoblastoid cell lines were prepared from HLA-D homozygous donors to yield homozygous cell lines (HCL), as described in detail by Nepom, et al. (PNAS 80: 6962-6966, 1980). Eighteen DR4-positive, three DR5-positive, one DRw12-positive, two DR8-positive, one DR9-positive, and one DR7-positive HCL were used, and are listed in Table 1. Each of these HCL was also HLA-DQw3 positive, except for two HCL (HAS-15 and KT-3) which express an undefined DQ antigen designated HCL-DQw-blank.

Digestion of Genomic DNA: Restriction endonuclease digestion of cellular DNA was performed at 37° C. with two or more units of Bam HI or Hind III (Bethesda Research Laboratories) per ug of DNA for 18 hours. Digestion was monitored for completeness by minigel analysis of both the genomic digest and of lambda DNA to which an aliquot of the genomic digestion mixture had been added. Reactions were stopped by addition of EDTA to a final concentration of 10 mM. DNA digests were concentrated by addition of ⅜ volume of 5M ammonium acetate and 2 volumes of ethanol. After chilling 30 minutes in a dry ice methanol bath the DNA was pelleted in a microfuge for 8 min. Pellets were resuspended in TE (10 mM Tris-HCL 1 mM EDTA).

Southern Blotting: Restriction endonuclease-digested DNA (12 ug/lane) was applied to 0.7% agarose gels in Tris-acetate-EDTA buffer. Lamdba DNA digested with Hind III, and $\phi$X 174 DNA digested with Hae III (Bethesda Research Laboratories) were included as molecular weight markers. Gels were run at 1.5 volts per centimeter for 17 hours, then stained with ethidium bromide. The gels were soaked 15 min in 0.25N HCl, followed by treatment with 0.5N NaOH, 1.5M NaCl for 1 hour to denature the DNA. Gels were neutralized by soaking 1 hour in 0.5M Tris, 3.0M NaCl, pH 7.0. The gels were then dried on a vacuum gel dryer at 65° C. The dried gel was then inserted into a polyethylene bag in the presence of a radiolabeled DNA probe.

Synthesis and Labeling of an Oligonucleotide Probe: A DNA probe was synthesized as DQ46 on an Applied Biosystems instrument according to the manufacturer's specifications. DQ46 was labeled with P32 using the polynucleotide kinase labeling procedure described in Maniatis, et Cloning: A laboratory manual, Cold Spring al. (Molecular Cloning: A Laboratory Manual, Cold Spring Laboratory, 1982). In this exchange reaction, an $\alpha$P32 is provided at the 5' termininus of the oligonucleotide.

Hybridization: $3 \times 10^7$ to $5 \times 10^7$ cpms of labeled oligonucleotide were diluted into 15-20 mls of 6X SSC and incubated with the dried gel in its polyethylene bag for 48 hours at 42° C. The dried gel was then removed, washed 3 times at room temperature in 2X SSC, 0.1% SDS for 5 minutes per wash, and 2 times at 62° C. in 2X SSC, 0.1% SDS for 20 minutes per wash. The dried gel was then exposed to x-ray film to reveal by autoradiography the presence of hybridizing bands (FIG. 3).

Figure 3:
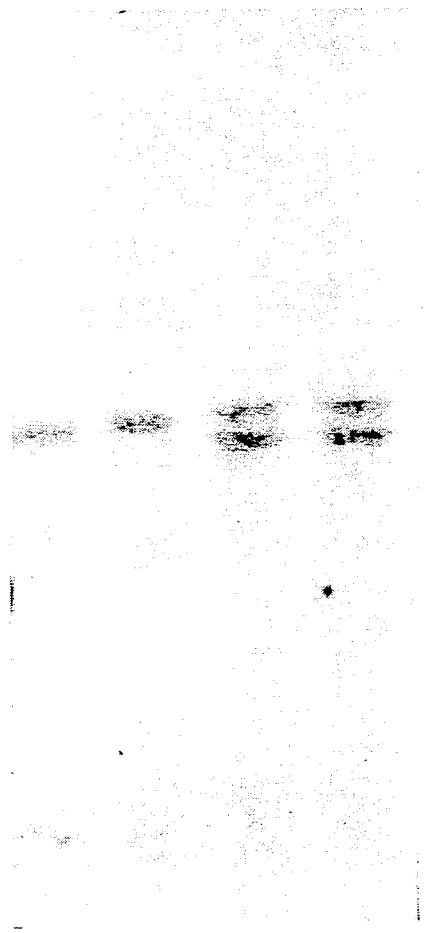
FIG. 3 depicts the hybridization pattern of restriction fragments generated from the DNA of DQw3.1 and DQw3.2 individuals.

As shown in FIGS. 2 and 3, using the restriction endonuclease Hind III, the presence of a 3.2 kb band in the absence of a 3.4 kb band is sufficient for the diagnosis of DQw3.2.

Example II

Serologic Detection of the DQw3.2 Allele

There are three general kinds of assays used to type human lymphocytes for HLA antigen expression. First, and the one most used at the present time, is complement-dependent lysis. Second are assays measuring binding of antibody to lymphocytes by enzyme-linked immunoassay (ELISA). Elements of the first method have been combined with standard format ELISA assays to develop a micro-ELISA assay suitable for HLA typing. The third uses a fluorescing compound to measure binding of antibody to lymphocytes.

The micro-ELISA method will be described in detail, and the other methods in brief, as illustrations of the use of these methods.

Micro-Enzyme-Linked Immunoabsorbent Assay (ELISA) to Detect Monoclonal Antibody Binding to HLA Antigens Determining DQw3.2

Terasaki microtrays are prepared by addition to each well of 5 ul of a 1 ug/ml solution of poly-L-lysine in phosphate-buffered saline (PBS). The plates are incubated at 37° C. for 1 hour and washed with PBS by immersion and decanting. Human leukocytes are dispensed into each well, 1 ul of a suspension of 1 to $5 \times 10^6$ cells per ml of RPMI-1640 medium without serum. The plates are centrifuged at 90 g for 3 minutes. A solution of 1% bovine serum albumin (BSA) in PBS with 0.2% azide is added to the plates, which are stored at 4° C. for 1 to 48 hours. Before adding antibody, the plates are washed three times.

In the indirect assay, monoclonal antibody P100.1, A10, and control are added to separate wells, 1 ul per well. After 1 hour at room temperature, the plates are washed five times and a solution of the F(ab')$_2$ fragment of anti-immunoglobulin coupled with horseradish peroxidase (HRP) is added, 5 ul per well. The plates are then incubated at room temperature for 30 to 60 minutes. In the direct assay, HRP is coupled to the monoclonal antibody; the second step is thus unnecessary. Antibodies coupled to HRP are diluted in a solution of 0.1% BSA in PBS without azide.

After treatment with antibody, the trays are washed five times. The presence of HRP-antibody complexes in the wells is visualized by the addition of a solution of substrate (hydrogen peroxide) and chromogen (OPD, Organon Diagnostics, West Orange, N.J.) or ABTS (Boehringer-Mannheim Biochemicals, Indianapolis, Ind.) in 0.1M sodium citrate/0.2 M sodium phosphate.

Color change in wells after 30 to 60 minutes incubation at room temperature indicates binding of monoclonal antibody to leukocytes in those wells.

Reactivity with 100.1 and no reactivity with A10 detects and defines the DQw3.2 allele.

Detection of the DQw3.2 Specificity Using Monoclonal Antibodies Labeled with Fluorescein Isothiocyanate (FITC) Using a Fluorescence-Activated Cell Sorter (FACS)

Monoclonal antibody isolated from ascites is conjugated to FITC according to the method of Goding (Goding, J. Immunol. Methods 13: 215, 1976). Cells to be analyzed are mixed with saturating amounts of FITC-conjugated antibody and incubated for 30 minutes at 4° C. Treated cells are washed and the amount of antibody bound assessed by comparing the fluorescence intensity (mean modal) of cells incubated with test and control antibodies on a FACS IV (Becton-Dickinson) fitted with a log amplifier.

Detection of the DQw3.2 Specificity Using a Complement-Mediated Microcytotoxicity Assay $10^3$–$10^4$ human leukocytes are dispensed into each well of a Terasaki microtray; 1 ul monoclonal antibodies 100.1, A10, and controls are added in the presence of heterologous (rabbit or guinea pig) complement. After incubation for 1 hour, the proportion of cells killed by the combination of specific antibody and complement is determined by eosin dye uptake and read visually through a microscope. Alternatively, the proportion of cells killed may be determined radiometrically or photometrically by release of bound ligand. Lysis of <50% of cells is evidence of positive reactivity. Reactivity of 100.1 but not A10 is evidence of the presence of DQw3.2.

Table 1 and Table 2 illustrate the results of DQw3.2 determinations in a population of homozygous typing cells and in a diabetic (IDDM) population.

TABLE 1

Genomic and serologic polymorphic variants among HLA-DQw3 cell lines homozygous for HLA-D

| HCL | HLA-D | HLA-DR | HLA-DQ | Monoclonal Antibody Reactivity P100.1 | A-10-83 | RFLP Bam HI 12 kb | Bam HI 6.9/3.7 kb | Hind III 3.4 kb |
|---|---|---|---|---|---|---|---|---|
| ER | Dw4 | DR4, w53 | DQw3 | + | + | − | + | + |
| WALK* | Dw4 | DR4, w53 | DQw3 | + | + | + | + | + |
| NIN | Dw4 | DR4, w53 | DQw3 | + | + | − | + | + |
| PRIESS | Dw4 | DR4, w53 | DQw3 | + | − | + | − | − |
| MJ-4 | Dw4 | DR4, w53 | DQw3 | + | − | + | − | − |
| EM | Dw10 | DR4, w53 | DQw3 | + | − | + | − | − |
| FS | Dw10 | DR4, w53 | DQw3 | + | − | + | − | − |
| JHa | Dw13 | DR4, w53 | DQw3 | + | + | − | + | + |
| SST | Dw13 | DR4, w53 | DQw3 | + | − | + | − | − |
| THO | Dw14 | DR4, w53 | DQw3 | + | − | + | − | − |
| BIN-40 | Dw14 | DR4, w53 | DQw3 | + | − | + | − | − |
| LS-40 | Dw14 | DR4, w53 | DQw3 | + | − | + | − | − |
| KT-2 | LD "KT2" | DR4, w53 | DQw3 | + | − | + | − | − |
| KT-13 | LD "KT2" | DR4, w53 | DQw3 | + | − | + | − | − |
| TAS | LD "TAS" | DR4, w53 | DQw3 | + | − | + | − | − |
| SWEIG | Dw5 | DR5, w52 | DQw3 | + | + | − | + | + |
| JGL | Dw5 | DR5, w52 | DQw3 | + | + | − | + | + |
| JME | Dw5 | DR5, w52 | DQw3 | + | + | − | + | + |
| HLF | DB6 | DRw12, w52 | DQw3 | + | + | − | + | + |
| 8854 | Dw8 | DRw8, w52 | DQw3 | + | + | − | + | + |
| LUY | Dw8 | DRw8, w52 | DQw3 | + | + | − | + | + |
| KOZ | DB5 | DRw9, w53 | DQw3 | + | − | + | − | − |
| JK | Dw11 | DR7, w53 | DQw3 | + | − | + | − | − |

*WALK, although homozygous for HLA-D, is heterozygous for the DQw3.1 and DQw3.2 alleles.

TABLE 2

Increase of DQw3.2 among HLA-DR4 diabetics compared to nondiabetics

|  | DQw3.1 | DQw3.2 |
|---|---|---|
| DR4 diabetics | 1/17 (6%) | 16/17 (94%) |

TABLE 2-continued

| Increase of DQw3.2 among HLA-DR4 diabetics compared to nondiabetics | | |
|---|---|---|
| | DQw3.1 | DQw3.2 |
| DR4 nondiabetics | 10/26 (38%) | 16/26 (62%) |

From the foregoing, it will be appreciated that, although specific embodiments of the invention have been described herein for purposes of illustration, various modifications may be made without deviating from the spirit and scope of the invention. Accordingly, the invention is not to be limited except as by the appended claims.

We claim:

1. A method for identifying an individual having the DQw3.2 haplotype associated with susceptibility to insulin-dependent diabetes mellitus comprising:

incubating a first monoclonal antibody with a portion of cells obtained form said individual, wherein said first monoclonal antibody is reactive with cell lines homozygous for HLA-DQw3.2 and with cell lines homozygous for HLA-DQw3.1, said respective cell lines having a BamHI restriction endonuclease fragment pattern comprising a 12Kb fragment or 6.9 Kb and 3.7 Kb fragments, said fragments detectable by a DNA probe substantially homologous with a fragment of the DQβ gene of the human major histocompatibility complex;

incubation a second monoclonal antibody with a separate portion of cells from said individual wherein said second monoclonal antibody is reactive with cell lines homozygous for HLA-DQw3.1 and having a BamHI restriction endonuclease pattern comprising 6.9 Kb and 3.7 Kb fragments, said fragments detectable by a DNA probe substantially homologous with a portion of the DQβ gene of the human major histocompatibility complex;

detecting the presence of immunocomplexes formed between said first monoclonal antibody and said individual's cells, and said second monoclonal antibody and said individual's cells; and determining from the results of the step of detection whether the DQw3.2 haplotype associated with susceptibility to diabetes is present.

2. The method of claim 1, wherein said first monoclonal antibody is P100.12, obtained from cell line ATCC HB 8822.

3. The method of claim 1 wherein said first and second monoclonal antibodies are labeled.

4. The method of claim 3 wherein said label is selected form the group consisting of enzymes, fluorophores, radioisotopes, and luminescers.

5. The method of claim 1 wherein the step of detecting is by enzyme reaction, fluorescence emission, luminescence emission or cell lysis.

6. The method of claim 1, wherein the cells obtained form said individual are leukocytes.

7. The method of claim 1, wherein the presence of said immune complexes is determined by a fluorescence activated cell sorter.

8. A method for identifying an individual having the DQw3.2 haplotype associated with susceptibility to insulin-dependent diabetes mellitus, comprising:

coating a portion of a surface with a first monoclonal antibody, wherein said first monoclonal antibody is reactive with cell lines homozygous for HLA-DQw3.2 and with cell lines homozygous for HLA-DQw3.1, said respective cell lines having a BamHI restriction endonuclease fragment pattern comprising a 12 Kb fragment, or 6.9 Kb and 3.7 Kb fragments, said fragments detectable by a DNA probe substantially homologous with a portion of the DQβ gene of the human major histocompatibility complex;

coating a portion of a surface with a second monoclonal antibody, wherein said second monoclonal antibody is reactive with cell lines homozygous for HLA-DQw3.1 and having a BamHI restriction endonuclease pattern comprising 6.9 Kb and 3.7 Kb fragments, said fragments detectable by a DNA probe substantially homologous with a portion of the DQβ gene of the human major histocompatibility complex;

reacting cells form said individual with both portions of said surface; and detecting the presence of cells bound to said portions of the surface and therefrom determining whether the DQw3.2 haplotype associated with susceptibility to diabetes is present.

9. The method of claim 8, wherein the first monoclonal antibody is P100.1, obtained from ATCC HB 8822.

10. The method of claim 8, wherein the presence of bound cells are detected by a protein stain or with a labeled antibody.

11. The method of claim 8, wherein the surface is a plastic or filter paper surface.

* * * * *